(12) United States Patent
Herron et al.

(10) Patent No.: US 7,074,534 B2
(45) Date of Patent: Jul. 11, 2006

(54) POLYMERIC CHARGE TRANSPORT COMPOSITIONS AND ELECTRONIC DEVICES MADE WITH SUCH COMPOSITIONS

(75) Inventors: Norman Herron, Newark, DE (US); Nora Sabina Radu, Landenberg, PA (US); Eric Maurice Smith, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 245 days.

(21) Appl. No.: 10/612,237

(22) Filed: Jul. 2, 2003

(65) Prior Publication Data

US 2004/0092687 A1     May 13, 2004

Related U.S. Application Data

(60) Provisional application No. 60/458,277, filed on Mar. 28, 2003, provisional application No. 60/394,767, filed on Jul. 10, 2002.

(51) Int. Cl.
*G03G 5/04* (2006.01)
*C07D 241/38* (2006.01)
*C08F 32/08* (2006.01)
*C08F 132/08* (2006.01)

(52) U.S. Cl. ............... 430/76; 430/96; 428/917; 544/349; 544/353; 548/428; 526/259

(58) Field of Classification Search ............ 252/299.01; 524/91, 260; 546/88; 552/101
See application file for complete search history.

(56) References Cited

U.S. PATENT DOCUMENTS 6,344,505 B1 *   2/2002   Valentine et al. ........... 524/91
   6,740,407 B1 *   5/2004   Usuki et al. .............. 428/408
2003/0197158 A1 * 10/2003   Lee et al. ................ 252/582

FOREIGN PATENT DOCUMENTS

FR            2099783    *   6/1970

OTHER PUBLICATIONS

Zhao et al., "Photorefractive Polymer with Side-Chain Second Order Nonlinear Optical and CHarge-Transporting Groups", Chem. Mater. 1995 (7), 1237-1242.*

Chao et al., "Effect of Side Chain Alkyl Length on the Electroluminescence Characteristics of Carbazole-Based Light Emitting Polymers", Macromol, Chem. Phys. 2001(202) 2864-2871.*

English abstract for FR-2099783 by Derwent, 1970.*

Leclerc, Mario et al., Electrochemical, Conductive, and Magnetic Properties of 2,7-Carbazole-Based Conjugated Polymers, Macromolecules, 2002, 2122-2128, 35, American Chemical Society.

Patent Abstracts of Japan, Publ. No. 61041152, Publ. Date Feb. 27, 1986, vol. 010, No. 198, Hitachi Chem. Co. Ltd.

Jin, Sung-Ho et al., Blue electroluminescence in blend of polymers containing carbazole and 1,3,4-oxadiazole units, Thin Solid Films, 2000, 255-258, 363, Elsevier Science, S.A.

Limburg, W. et al., Electronic Transport Properties of Molecularly Doped Polymers—Some Substituted Triarylmethanes, Organic Coatings and Plastics Chemistry, 1978, 534-539, vol. 38.

Rehahn, Matthias et al, Synthesis, solution properties and conversion of poly(2,9-o-phenanthroline-alt-(2',5'-dihexyl)-4,4"-p-terphenylene)s into soluble, well-defined copper(I) and silver (I) complex polymers, Macromol. Chem. Phys., 1998. 127-140, 199, Huthig & Wepf Verlag, Zug.

Yamamoto, Takakazu et al., Preparation and Properties of π-Conjugated Poly(1,10-phenanthroline03,8-diyl), Chemistry Letters, 1995, 785-786.

Yamamoto, Takakazu et al., Preparation of New Electron-Accepting π-Conjugated Polyquinoxalines. Chemical and Electrochemical Reduction, Electrically Conducting Properties, and Use in Light-Emitting Diodes, J. Am. Chem. Soc., 1996, 3930-3937, 18, American Chemical Society.

O'Brien, D. et al., Use of poly(phenyl quinoxaline) as an electron transport material in polymer light-emitting diodes, Appl. Phys. Lett., Aug. 12, 1996, 881-883, 69(7), American Institute of Physics.

Giebeler, C. et al., The photovoltaic effect in poly(p-phenylene-2,3'-bis(3,2'-diphenyl)-quinoxaline-7-7'-diyl), Optical Materials, Jan. 1998, 99-103, 9, Elsevier Science B.V.

* cited by examiner

*Primary Examiner*—Shean C Wu
(74) *Attorney, Agent, or Firm*—John H. Lamming

(57) ABSTRACT

The present invention relates to polymeric charge transport compositions. The invention further relates to electronic devices in which there is at least one active layer comprising such charge transport compositions.

4 Claims, 7 Drawing Sheets

I(a)

I(b)

I(c)

II(a)

II(b)

II(c)

III(a)

III(b)

III(c)

III(d)

IV(a)

IV(b)

IV(c)

IV(d)

IV(e)

IV(f)

V(a)

V(b)

V(c)

V(d)

V(e)

POLYMERIC CHARGE TRANSPORT COMPOSITIONS AND ELECTRONIC DEVICES MADE WITH SUCH COMPOSITIONS

CROSS REFERENCE TO RELATED APPLICATIONS

This application claims priority from U.S. Provisional Application Ser. No. 60/394,767, filed Jul. 10, 2002, and U.S. Provisional Application Ser. No. 60/458,277, filed Mar. 28, 2003.

BACKGROUND OF THE INVENTION

1. Field of the Invention

The present invention relates to polymeric charge transport compositions. The invention further relates to electronic devices in which there is at least one active layer comprising such charge transport compositions.

2. Background

In organic photoactive electronic devices, such as light-emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices which use photoactive materials, frequently include one or more charge transport layers, which are positioned between the photoactive (e.g., light-emitting) layer and one of the contact layers. A hole transport layer may be positioned between the photoactive layer and the hole-injecting contact layer, also called the anode. An electron transport layer may be positioned between the photoactive layer and the electron-injecting contact layer, also called the cathode.

There is a continuing need for charge transport materials.

SUMMARY OF THE INVENTION

The present invention is directed to a charge transport composition which is an oligomer or polymer. As used herein, the scope of the term "polymer" is intended to include polymer and oligomers having one or more different types of monomeric units, and is intended to mean compounds having at least two repeating monomeric units. The term "polymeric" is intended to have the same scope as polymer.

In one embodiment, the present invention is directed to a polymeric charge transport composition having at least one first monomeric unit having Formula I(a), in FIG. 1, wherein:

$Ar^1$ can be the same or different at each occurrence and is selected from aryl and heteroaryl;

$Ar^2$ can be the same or different at each occurrence and is selected from arylene and heteroarylene;

$R^1$ can be the same or different at each occurrence and is selected from H, alkyl, heteroalkyl, aryl, heteroaryl, arylalkylene, heteroarylalkylene, $C_nH_aF_b$, and $C_6H_cF_d$; or adjacent $R^1$ groups can be joined to form 5- or 6-membered rings;

n is an integer; and a, b, c, and d are 0 or an integer such that a+b=2n+1, and c+d=5.

In one embodiment, the present invention is directed to a polymeric charge transport composition having at least one first monomeric unit having Formula I(b) wherein:

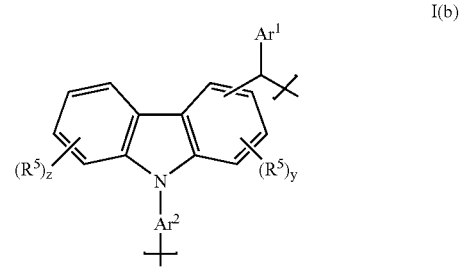

I(b)

$Ar^1$ can be the same or different at each occurrence and is selected from aryl and heteroaryl;

$Ar^2$ can be the same or different at each occurrence and is selected from arylene and heteroarylene;

$R^5$ is the same or different at each occurrence and is selected from H, F, Cl, Br, hydroxyl, carboxyl, carbonyl, silyl, siloxyl, alkyl, heteroalkyl, alkenyl, alkynyl, aryl, heteroaryl, alkylenearyl, alkenylaryl, alkynylaryl, alkyleneheteroaryl, alkenylheteroaryl, alkynylheteroaryl, $C_nH_aF_b$, $OC_nH_aF_b$, $C_6H_cF_d$, and $OC_6H_cF_d$, or both of $R^5$ together may constitute an arylene or heteroarylene group;

a, b, c, and d are 0 or an integer such that a+b=2n+1, and c+d=5, n is an integer (as above);

y is 0 or an integer from 1 through 3; and z is 0 or an integer from 1 through 4.

In one embodiment, the present invention is directed to a polymeric charge transport composition having at least one first monomeric unit having Formula I(c), in FIG. 1, wherein:

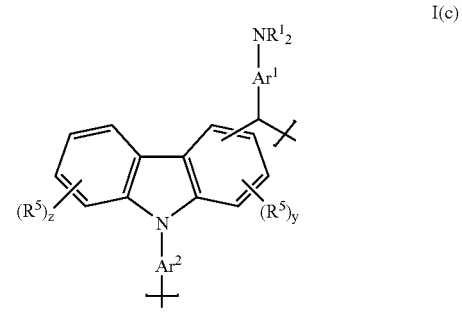

I(c)

$Ar^1$ can be the same or different at each occurrence and is selected from aryl and heteroaryl;

$Ar^2$ can be the same or different at each occurrence and is selected from arylene and heteroarylene;

$R^1$ can be the same or different at each occurrence and is selected from H, alkyl, heteroalkyl, aryl, heteroaryl, arylalkylene, heteroarylalkylene, $C_nH_aF_b$, and $C_6H_cF_d$; or adjacent $R^1$ groups can be joined to form 5- or 6-membered rings;

$R^5$ is the same or different at each occurrence and is selected from H, F, Cl, Br, hydroxyl, carboxyl, carbonyl, silyl, siloxyl, alkyl, heteroalkyl, alkenyl, alkynyl, aryl, heteroaryl, alkylenearyl, alkenylaryl, alkynylaryl, alkyleneheteroaryl, alkenylheteroaryl, alkynylheteroaryl, $C_nH_aF_b$, $OC_nH_aF_b$, $C_6H_cF_d$, and $OC_6H_cF_d$, or both of $R^5$ together may constitute an arylene or heteroarylene group;

a, b, c, and d are 0 or an integer such that a+b=2n+1, and c+d=5, n is an integer (as above);

y is 0 or an integer from 1 through 3; and z is 0 or an integer from 1 through 4.

In one embodiment, the present invention is directed to a polymeric charge transport composition having at least one first monomeric unit selected from Formulae II(a), II(b), and II(c) in FIG. 2, wherein:

$R^2$ and $R^3$ are the same or different at each occurrence and are selected from H, F, Cl, Br, alkyl, heteroalkyl, alkenyl, alkynyl, aryl, heteroaryl, $C_nH_aF_b$, $OC_nH_aF_b$, $C_6H_cF_d$, and $OC_6H_cF_d$;

$R^4$ is the same or different at each occurrence and is selected from alkylene, heteroalkylene, alkenylene, arylene, heteroarylene, alkynylene, or arylenealkynylene;

a, b, c, and d are 0 or an integer such that a+b=2n+1, and c+d=5, n is an integer;

p is 0 or 1;

x is 0, 1 or 2; and y is 0 or an integer from 1 through 3.

In one embodiment, the present invention is directed to a polymeric charge transport composition having at least one first monomeric unit selected from Formulae II(a), II(b), and II(c) in FIG. 2, as described above, and wherein there is at least one substitute on an aromatic group selected from F, $C_nH_aF_b$, $OC_nH_aF_b$, $C_6H_cF_d$, and $OC_6H_cF_d$.

In one embodiment, the present invention is directed to a polymeric charge transport composition having at least one first monomeric unit selected from Formulae III(a), III(b), III(c), and III(d) as shown in the drawings in FIG. 3, wherein:

$R^4$ is the same or different at each occurrence and is selected from alkylene, heteroalkylene, alkenylene, arylene, heteroarylene or arylenealkynylene;

$R^5$ is the same or different at each occurrence and is selected from H, F, Cl, Br, hydroxyl, carboxyl, carbonyl, silyl, siloxyl, alkyl, heteroalkyl, alkenyl, alkynyl, aryl, heteroaryl, alkylenearyl, alkenylaryl, alkynylaryl, alkyleneheteroaryl, alkenylheteroaryl, alkynylheteroaryl, $C_nH_aF_b$, $OC_nH_aF_b$, $C_6H_cF_d$, and $OC_6H_cF_d$, or both of $R^5$ together may constitute an arylene or heteroarylene group;

a, b, c, and d are 0 or an integer such that a+b=2n+1, and c+d=5, n is an integer;

x is 0, 1, or 2;

y is 0 or an integer from 1 through 3; and z is 0 or an integer from 1 through 4.

In one embodiment, the present invention is directed to a polymeric charge transport composition having at least one first monomeric unit having Formula I(a), I(b), and I(c) in FIG. 1 and at least one second monomeric unit selected from Formulae II(a) through II(c) in FIG. 2 and Formulae III(a), III(b), III(c), and III(d) in FIG. 3, as described above.

In one embodiment, the present invention is directed to an electronic device having at least one active layer comprising a polymer having at least one first monomeric unit selected from Formulae I(a), I(b), I(c), II(a), II(b), II(c), III(a), III(b), III(c), and III(d) shown in FIGS. 1 through 3, wherein $Ar^1$, $Ar^2$, $R^1$ through $R^5$, a through d, n, p, and x through z are as defined above.

In one embodiment, the present invention is directed to an electronic device having at least one active layer comprising a polymer having at least one first monomeric unit having Formula I(a), I(b), and I(c) in FIG. 1 and at least one second monomeric unit selected from Formulae II(a) through II(c) in FIG. 2 and Formulae III(a), III(b), III(c), and III(d) in FIG. 3, as described above.

As used herein, the term "charge transport composition" is intended to mean material that can receive a charge from an electrode and facilitates movement through the thickness of the material with relatively high efficiency and small loss of charge. Hole transport compositions are capable of receiving a positive charge from an anode and transporting it. Electron transport compositions are capable of receiving a negative charge from a cathode and transporting it. The term "anti-quenching composition" is intended to mean a material which prevents, retards, or diminishes both the transfer of energy and the transfer of an electron from the excited state of the photoactive layer. The term "photoactive" refers to any material that exhibits electroluminescence, photoluminescence, and/or photosensitivity. The term "HOMO" refers to the highest occupied molecular orbital of a compound. The term "LUMO" refers to the lowest unoccupied molecular orbital of a compound. The term "group" is intended to mean a part of a compound, such as a substitute in an organic compound. The prefix "hetero" indicates that one or more carbon atoms has been replaced with a different atom. The term "alkyl" is intended to mean a group derived from an aliphatic hydrocarbon having one point of attachment, which group may be unsubstituted or substituted. The term "heteroalkyl" is intended to mean a group derived from an aliphatic hydrocarbon having at least one heteroatom and having one point of attachment, which group may be unsubstituted or substituted. The term "alkylene" is intended to mean a group derived from an aliphatic hydrocarbon and having two or more points of attachment. The term "heteroalkylene" is intended to mean a group derived from an aliphatic hydrocarbon having at least one heteroatom and having two or more points of attachment. The term "alkenyl" is intended to mean a group derived from a hydrocarbon having one or more carbon-carbon double bonds and having one point of attachment, which group may be unsubstituted or substituted. The term "alkynyl" is intended to mean a group derived from a hydrocarbon having one or more carbon-carbon triple bonds and having one point of attachment, which group may be unsubstituted or substituted. The term "alkenylene" is intended to mean a group derived from a hydrocarbon having one or more carbon-carbon double bonds and having two or more points of attachment, which group may be unsubstituted or substituted. The term "alkynylene" is intended to mean a group derived from a hydrocarbon having one or more carbon-carbon triple bonds and having two or more points of attachment, which group may be unsubstituted or substituted. The terms "heteroalkenyl", "heteroalkenylene", "heteroalkynyl" and "heteroalkynlene" are intended to mean analogous groups having one or more heteroatoms The term "heteroalkylene" is intended to mean a group derived from an aliphatic hydrocarbon having at least one heteroatom and having two or more points of attachment. The term "aryl" is intended to mean a group derived from an aromatic hydrocarbon having one point of attachment, which group may be unsubstituted or substituted. The term "heteroaryl" is intended to mean a group derived from an aromatic group having at least one heteroatom and having one point of attachment, which group may be unsubstituted or substituted. The term "arylalkylene" is intended to mean a group derived from an alkyl group having an aryl substitute, which group may be further unsubstituted or substituted. The term "heteroarylalkylene" is intended to mean a group derived from an alkyl group having a heteroaryl substitute, which group may be further unsubstituted or substituted. The term "arylene" is intended to mean a group derived from an aromatic hydrocarbon having two points of attachment, which group may be unsubstituted or substituted. The term "heteroarylene" is intended to mean a group derived from an aromatic group having at least one heteroatom and having two points of attachment, which group may be unsubstituted or substituted. The term "arylenealkylene" is intended to mean a group having both aryl and alkyl groups and having one point of attachment on an aryl group and one point of attachment on an alkyl group. The term "heteroarylenealkylene" is intended to mean a group having both aryl and alkyl groups and having one point of attachment on an aryl group and one point of attachment on an alkyl group, and in which there is at least one heteroatom. Unless otherwise indicated, all groups can be unsubstituted or substituted. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "complex", when used as a noun, is intended to mean a compound having at least one metallic ion and at least one ligand. In addition, the IUPAC numbering system is used throughout, where the groups from the Periodic Table are numbered from left to right as 1 through 18 (CRC Handbook of Chemistry and Physics, 81$^{st}$ Edition, 2000).

Unless otherwise defined, all technical and scientific terms used herein have the same meaning as commonly understood by one of ordinary skill in the art to which this invention belongs. Unless otherwise defined, all letter symbols in the figures represent atoms with that atomic abbreviation. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE PREFERRED EMBODIMENTS

Figure 1A:
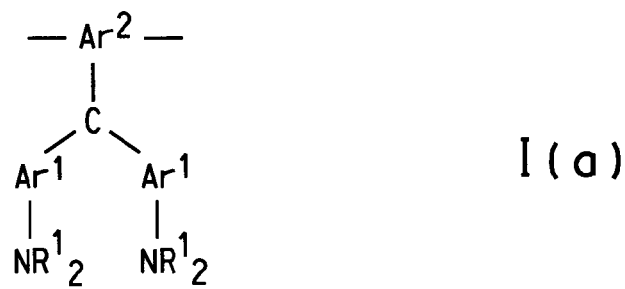
FIGS. 1A, 1B, and 1C show Formulae I(a), I(b) and I(c) for a charge transport monomeric unit.

The polymeric compositions of the invention are useful as charge transport materials. They can be used alone or with other materials. They can be used as hosts for photoactive materials.

Polymers with triarylmethane-derivative monomeric units having Formulae I(a) through I(c), are particularly useful as hole transport materials.

In general, n is an integer. In one embodiment, n is an integer from 1 through 20. In one embodiment, n is an integer from 1 through 12.

In one embodiment, $Ar^1$ is selected from phenyl and biphenyl groups, which may have one or more carbon atoms replaced with a heteroatom. All of these groups may further be substituted. Examples of substituents include, but are not limited to, alkyl, heteroalkyl, aryl, heteroaryl, arylalkylene, heteroarylalkylene, $C_nH_aF_b$, and $C_6H_cF_d$, where a through d and n are as defined above.

In one embodiment, $Ar^2$ is selected from phenylene and phenylenealkylene, which may be further substituted.

In one embodiment, $N(R^1)_2$ is a fused heteroaromatic ring group. Examples of such groups include, but are not limited to, carbazoles, benzodiazoles, and benzotriazoles.

In one embodiment $R^1$ is selected from alkyl groups having 1 through 12 carbon atoms, phenyl and benzyl.

Polymers with phenanthroline-derivative monomeric units having Formulae II(a) through II(c), are particularly useful as electron transport materials and anti-quenching materials.

In one embodiment, $R^2$ is selected from phenyl, biphenyl, pyridyl, and bipyridyl, which may further be substituted. Examples of substituents include, but are not limited to, alkyl, heteroalkyl, aryl, heteroaryl, arylalkylene, heteroarylalkylene, F, $C_nH_aF_b$, $OC_nH_aF_b$, $C_6H_cF_d$, and $OC_6H_cF_d$, where a through d and n are as defined above.

In one embodiment, at least one $R^2$ is selected from phenyl and biphenyl, and further substituted with a group selected from F, $C_nH_aF_b$, $OC_nH_aF_b$, $C_6H_cF_d$, and $OC_6H_cF_d$, where a through d and n are as defined above.

In one embodiment, $R^3$ is selected from alkyl groups having from 1 through 12 carbon atoms.

In one embodiment, $R^4$ is selected from phenylene, phenylenealkylene, alkylene and alkenylene.

In one embodiment, there is at least one substitutent on an aromatic ring selected from F, $C_nH_aF_b$, $OC_nH_aF_b$, $C_6H_cF_d$, and $OC_6H_cF_d$, where a through d and n are as defined above.

In general, n is an integer. In one embodiment, n is an integer from 1 through 20. In one embodiment, n is an integer from 1 through 12.

Polymers with quinoxaline-derivative monomeric units having Formulae III(a), III(b), III(c), and III(d) and wherein such polymers are not homopolymers, are particularly useful as electron transport materials and anti-quenching materials.

In general, n is an integer. In one embodiment, n is an integer from 1 through 20. In one embodiment, n is an integer from 1 through 12.

In one embodiment, $R^4$ is selected from phenylene, phenylenealkylene, alkylene and alkenylene.

In one embodiment, $R^5$ is selected from phenylalkenyl and phenylakynyl groups, which may be further substituted.

In one embodiment, $R^5$ is selected from alkylacetate and arylcarbonyl groups, which may be further substituted.

In one embodiment, $R^5$ is selected from alkyl groups having 1 through 12 carbon atoms.

In one embodiment, $R^5$ is selected from phenyl groups, substituted phenyl groups, pyridyl groups, and substituted pyridyl groups. The substitute can be selected from F, Cl, Br, hydroxyl, carboxyl, carbonyl, silyl, siloxyl, alkyl, heteroalkyl, alkenyl, alkynyl, aryl, heteroaryl, alkylenearyl, alkenylaryl, alkynylaryl, alkyleneheteroaryl, alkenylheteroaryl, alkynylheteroaryl, $C_nH_aF_b$, $OC_nH_aF_b$, $C_6H_cF_d$, and $OC_6H_cF_d$.

In one embodiment, two adjacent $R^5$ together are a biarylene group, which may be further substituted. In one embodiment, the biarylene group is selected from biphenylene and bipyridinylene. The substitute can be selected from F, Cl, Br, hydroxyl, carboxyl, cabonyl, silyl, siloxyl, alkyl, heteroalkyl, alkenyl, alkynyl, aryl, heteroaryl, alkylenearyl, alkenylaryl, alkynylaryl, alkyleneheteroaryl, alkenylheteroaryl, alkynylheteroaryl, $C_nH_aF_b$, $OC_nH_aF_b$, $C_6H_cF_d$, and $OC_6H_cF_d$.

Figure 1B:
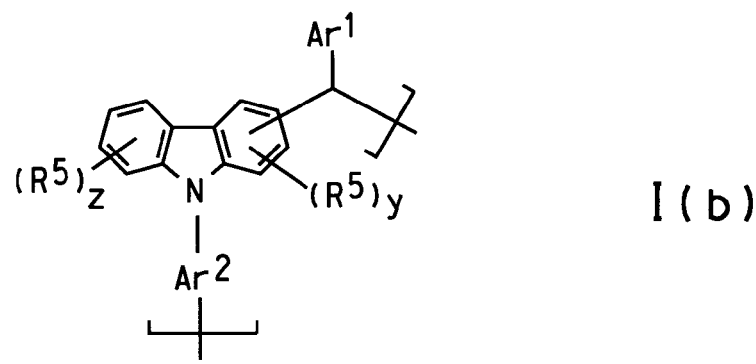
Figure 1C:
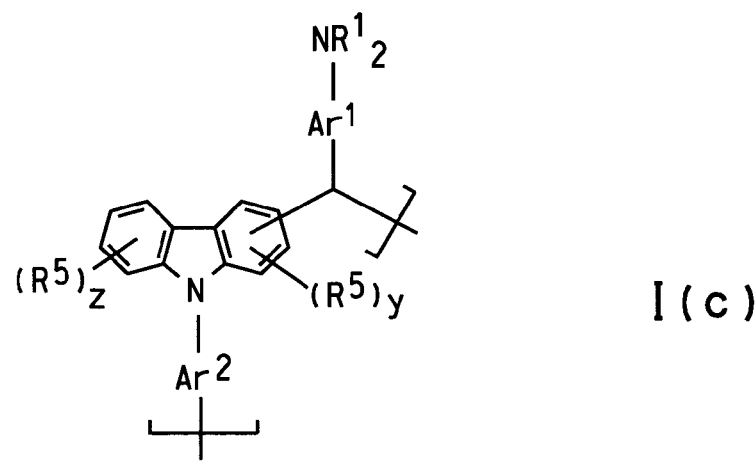
Figure 2A:
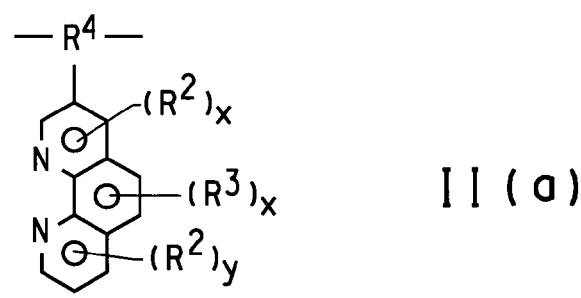
FIGS. 2A, 2B, and 2C, show Formulae II(a) through II(c) for a charge transport monomeric unit.
Figure 2B:
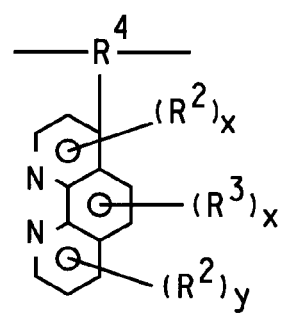
Figure 2C:
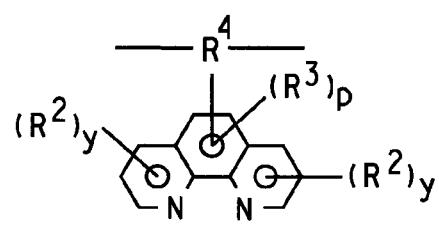
Figure 3A:
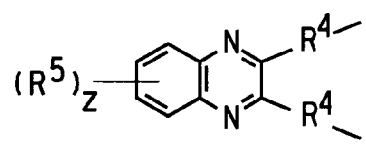
FIGS. 3A, 3B, 3C, and 3D show Formulae III(a), III(b), III(c) and III(d) for a charge transport monomeric unit.
Figure 3B:
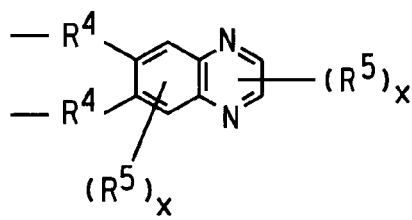
Figure 3C:
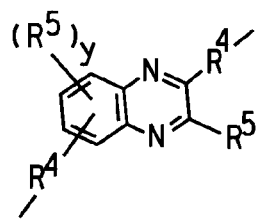
Figure 3D:
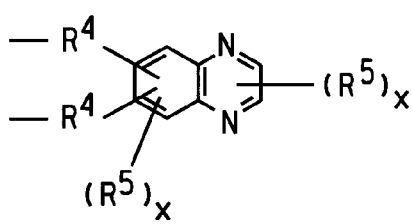
Figure 4A:
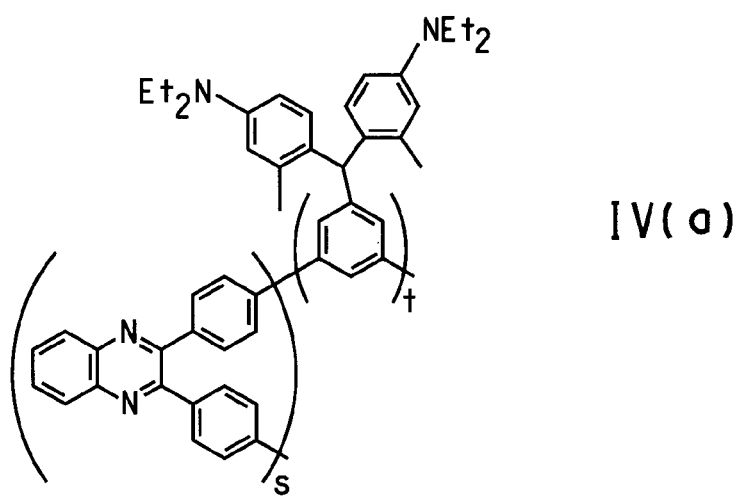
FIGS. 4A, 4B, 4C, 4D, 4E, and 4F show Formulae IV(a) through IV(f) for a polymeric charge transport composition of the invention.
Figure 4B:
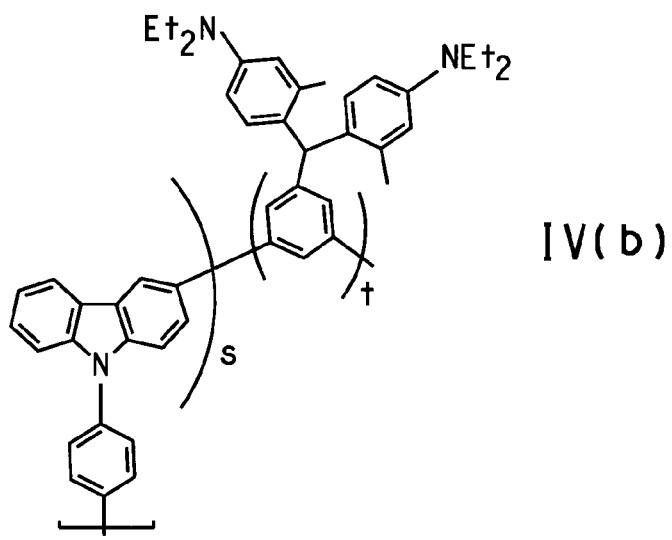
Figure 4C:
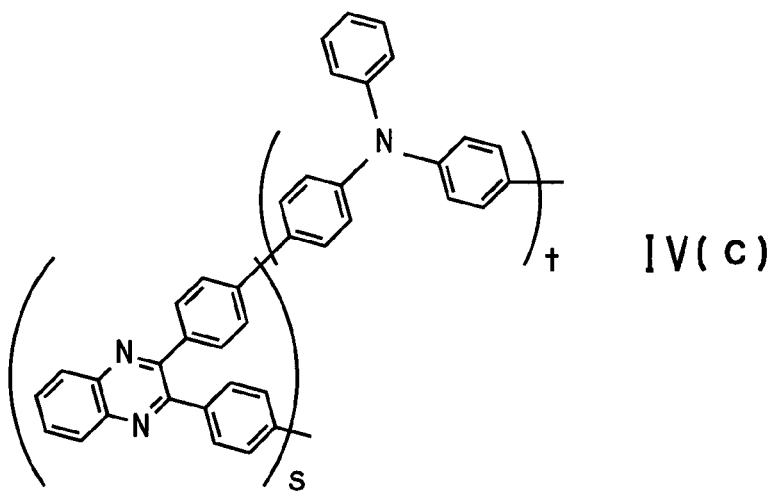
Figure 4D:
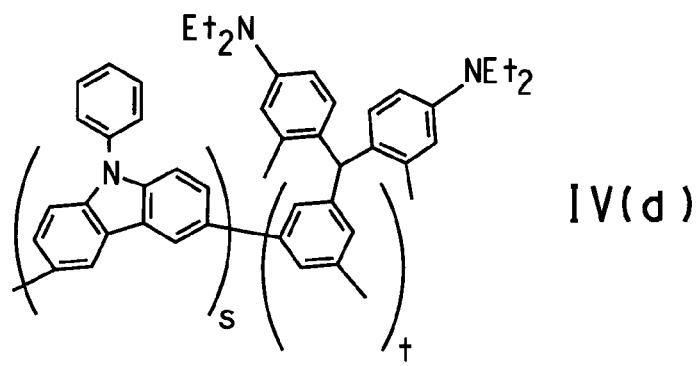
Figure 4E:
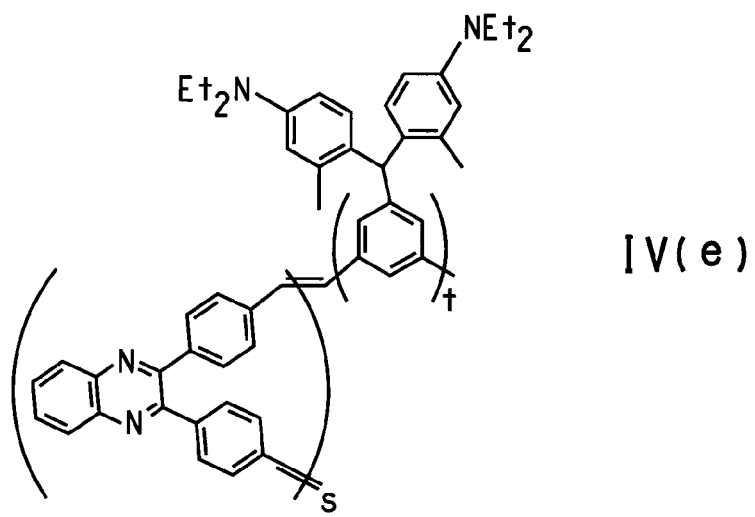
Figure 4F:
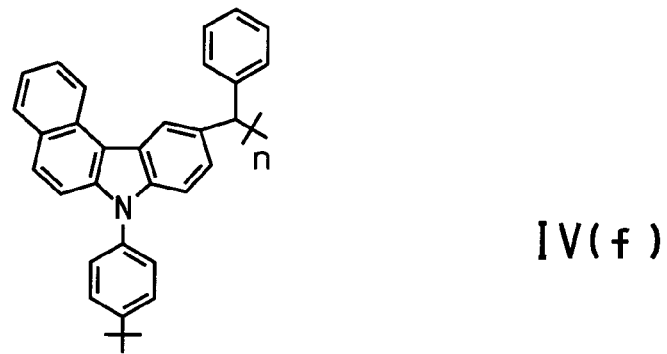

It is also possible to use both hole and electron transporting monomeric units in a polymeric structure. In one embodiment, a mixed charge transport material comprises a polymer having at least one first monomeric unit Formulae I(a) through I(c) in FIG. 1 and at least one second monomeric unit selected from Formulae II(a) through II(c) in FIG. 2 and Formulae III(a), III(b), III(c), and III(d) in FIG. 3.

The hole and electron transport monomeric units can be polymerized with like monomeric units to form homopolymers. They also can be polymerized with one or more different monomeric units to form copolymers. The hole and electron transport monomeric units can be copolymerized with each other or with other monomeric units, such as triarylamines, fluorenes, phenylenes, phenylenevinylenes, oxadiazoles, thiadiazoles, triazoles, carbazoles, and the like. Examples of oligomeric or polymeric hole and electron transport materials include, but are not limited to those shown in FIG. 4, Formulae IV(a) through IV(f), where:

s and t can be the same or different and are integers of 1 or more.

The polymers can be prepared using known synthetic techniques such as Suzuki or Yamamoto coupling reactions, as further described in the examples.

The compounds of the invention can be applied as thin films by evaporative techniques or conventional solution processing methods. As used herein, "solution processing" refers to the formation of films from a liquid medium. The liquid medium can be in the form of a solution, a dispersion, an emulsion, or other forms. Typical solution processing techniques include, for example, solution casting, drop casting, curtain casting, spin-coating, screen printing, inkjet printing, gravure printing,and the like.

Electronic Device

Figure 5A:
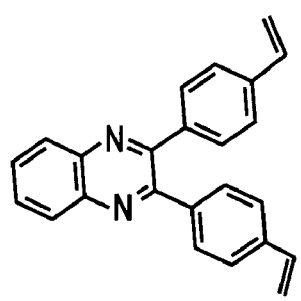
FIGS. 5A and 5B show starting materials 5a and 5b for a polymeric charge transport material and are 2,3-bis(4-vinylphenyl)quinoxaline and bis [4-(N,N-diethylamino)-2-methylphenyl]-(3,5-dibromophenyl)methane, respectively.
Figure 5B:
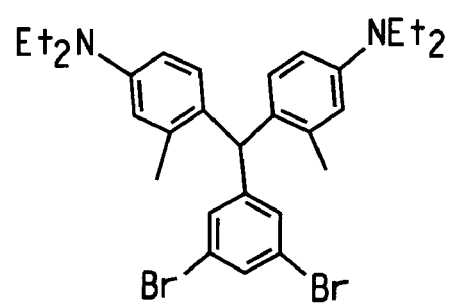
Figure 5C:
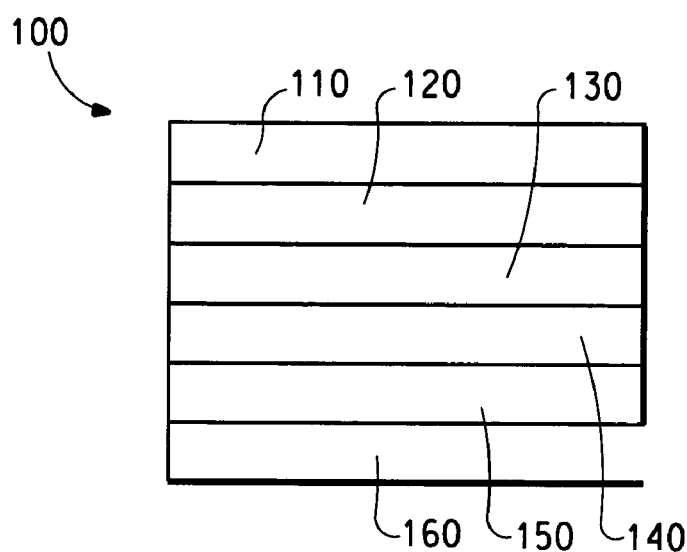
FIG. 5C is a schematic diagram of a light-emitting diode (LED).
Figure 6A:
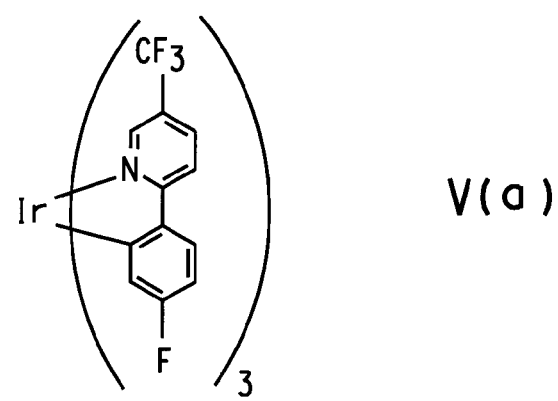
FIGS. 6A, 6B, 6C, 6D, and 6E show Formulae V(a) through V(e) for electroluminescent iridium complexes.
Figure 6B:
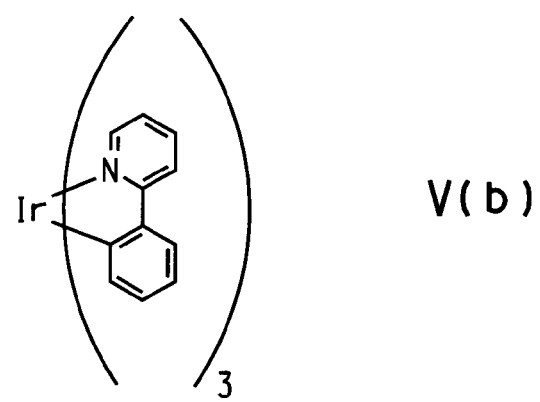
Figure 6C:
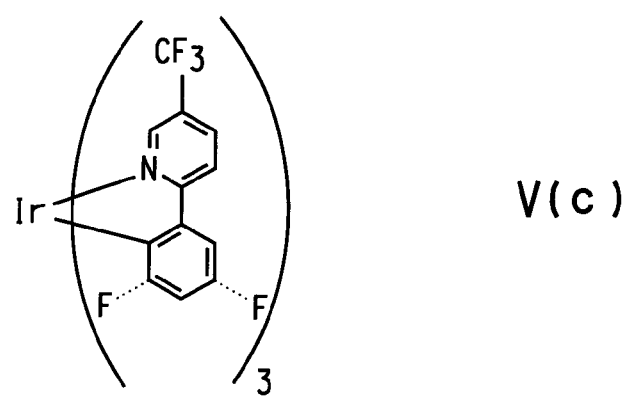
Figure 6D:
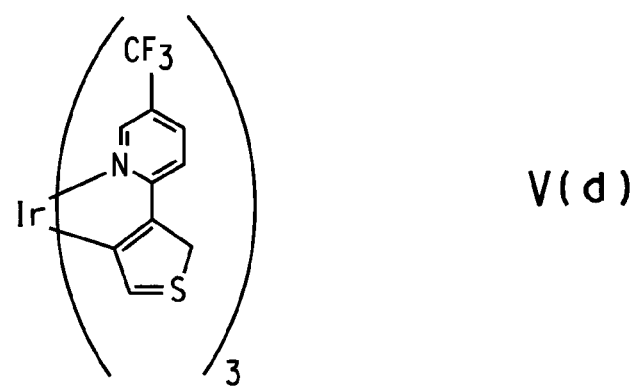
Figure 6E:
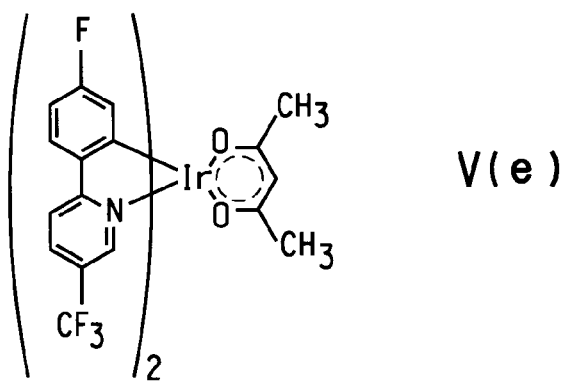

The present invention also relates to an electronic device comprising at least one of the charge transport compositions of the invention positioned between a photoactive layer and one electrode. A typical device structure is shown in FIG. 5. The device 100 has an anode layer 110 and a cathode layer 160. Adjacent to the anode is a layer 120 comprising hole transport material. Adjacent to the cathode is a layer 140 comprising an electron transport and/or anti-quenching material. Between the hole transport layer and the electron transport/anti-quenching layer is the photoactive layer 130. As an option, devices frequently use another electron transport layer 150, next to the cathode. Layers 120, 130, 140, and 150 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8–10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," *Nature* vol. 357, pp 477–479 (11 Jun. 1992). At least one of the anode and cathode should be at least partially transparent to allow the generated light to be observed.

The triarymethane derivative polymers of the invention, Formulae I(a) through I(c), are particularly useful as the hole transport composition in layer 120.

Examples of other hole transport materials which may be used for layer 120 have been summarized, for example, in Kirk-Othmer Encyclopedia of Chemical Technology, Fourth Edition, Vol. 18, p. 837–860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4tolylamino)phenyl]cyclohexane (TAPC), N,N'-bis(4-methylphenyl)-N,N'-bis(4-ethylphenyl)-[1,1'-(3,3'-dimethyl)biphenyl]-4,4-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), and porphyrinic compounds, such as copper phthalocyanine. Commonly used hole transporting polymers are polyvinylcarbazole, (phenylmethyl)polysilane, and polyaniline and mixtures thereof. It is also possible to obtain hole transporting polymers by doping hole transporting molecules such as those mentioned above into polymers such as polystyrene and polycarbonate.

Examples of the photoactive layer 130 include all known electroluminescent materials. Organometallic electroluminescent compounds are preferred. The most preferred compounds include cyclometalated iridium and platinum electroluminescent compounds and mixtures thereof. Complexes of Iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1–3), 379–383, and Campbell et al., in Phys. Rev. B, Vol. 65 085210. Examples of a few suitable iridium complexes are given in FIG. 6, as Formulae V(a) through V(f). Analogous tetracoordinated platinum complexes can also be used. These electroluminescent complexes can be used alone, or doped into charge-carrying hosts, as noted above. The polymeric charge transport materials of the invention can be used as hosts for organometallic and other emitters.

The phenanthroline derivative and quinoxaline derivative polymers of the invention, Formulae II(a) through II(c), III(a) through III(d), are particularly useful as the electron transport/anti-quenching composition in layer 140, or as electron transport composition in layer 150. Preferably the phenanthroline derivative and quinoxaline derivative polymers of the invention are used as the electron transport/anti-quenching layer in light emitting diode.

Examples of additional electron transport materials which can be used in layer 150 include metal chelated oxinoid compounds, such as tris(8-hydroxyquinolato)aluminum ($Alq_3$); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and mixtures thereof.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole transport layer 120, the electron transport layers 140 and 150, and cathode layer 160, may be surface treated to increase charge carrier transport efficiency. The choice of materials for each of the component layers is preferably determined by balancing the goals of providing a device with high device efficiency while providing adequate device longevity.

It is understood that each functional layer may be made up of more than one layer.

The device can be prepared by a variety of techniques, including sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be liquid processed from suitable solvents, using any conventional coating technique, including, but not limited to, spin-coating, dip-coating, roll-to-roll techniques, ink-jet printing, screen printing and gravure printing. In general, the different layers will have the following range of thicknesses: anode 110, 500–5000 Å, preferably 1000–2000 Å; hole transport layer 120, 50–2000 Å, preferably 200–1000 Å; photoactive layer 130, 10–2000 Å, preferably 100–1000 Å; electron transport layer 140 and 150, 50–2000 Å, preferably 100–1000 Å; cathode 160, 200–10000 Å, preferably 300–5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

The triarylmethane, phenanthroline derivative, and quinoxaline derivative polymers of the invention may be useful in applications other than OLEDs. For example, these compositions may be used in photovoltaic devices for solar energy conversion. They may also be used in field effect transistor for smart card and thin film transistor (TFT) display driver applications.

EXAMPLES

The following examples illustrate certain features and advantages of the present invention. They are intended to be illustrative of the invention, but not limiting. All percentages are by weight, unless otherwise indicated.

Example 1

This example illustrates the preparation of polymer IV(c) shown in FIG. 4.

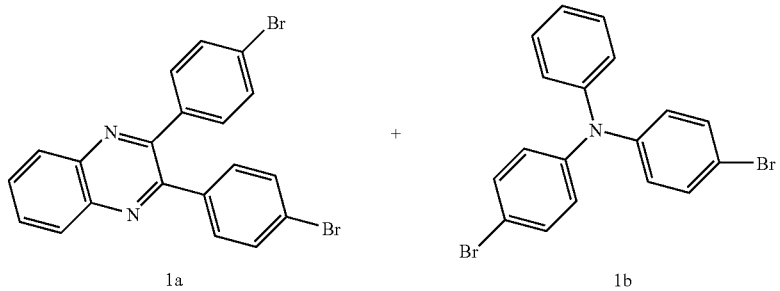

1a                                    1b

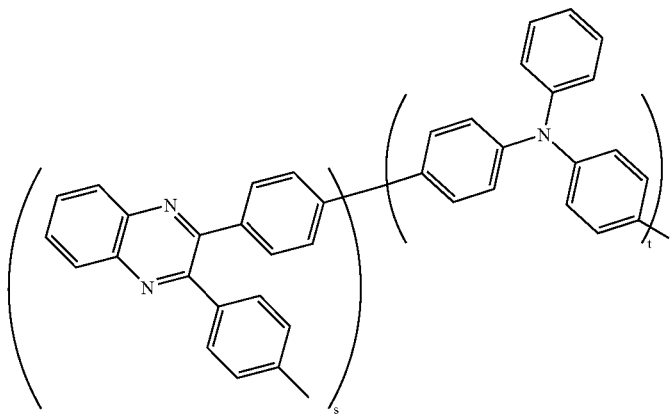

IV(c)

Under nitrogen, to a mixture of 1a (3.96 g, 9 mmol), 1b (3.63 g, 9 mmol), zinc (4.0 g, 61.2 mmol), $NiCl_2$ (0.234 g, 1.80 mmol), $PPh_3$ (1.87 g, 7.2 mmol) and bipyridine (0.29 g, 1.8 mmol) will be added DMF (100 mL). The resulting mixture will be heated to 90 C for 48 h. It will then be cooled to room temperature and diluted with $CH_2Cl_2$. After filtration, the solid will be washed with $CH_2Cl_2$ and the combined organic layer will be washed with 1N HCl and brine. The solution will be concentrated and precipitated from MeOH to give polymer IV(c).

Example 2

This example illustrates the preparation of polymer IV(a) shown in FIG. 4.

Polymer IV(a) will be made similarly to the polymerization procedure outlined for polymer IV(c).

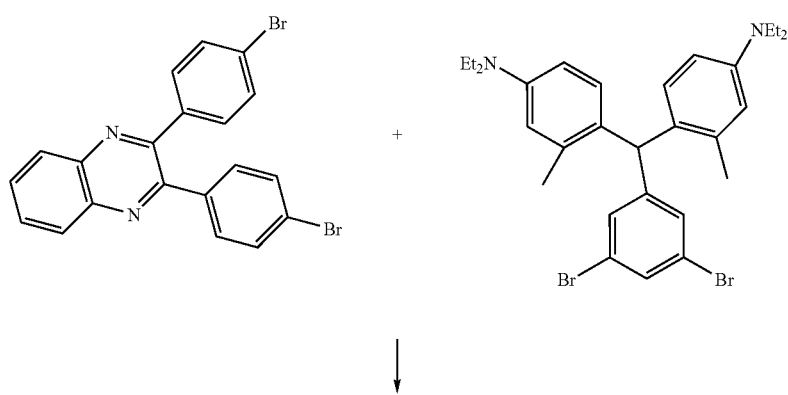

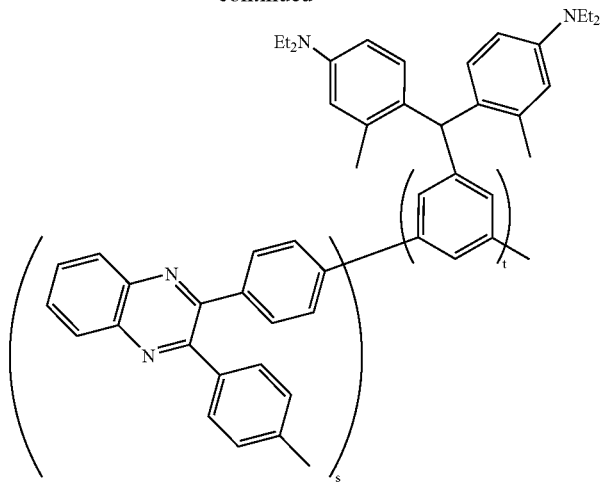
IV(a)
Example 3
This example illustrates the preparation of polymer IV(d), shown in FIG. 4.
Polymer IV(d) will be made similarly to polymerization procedure outlined for polymer IV(c).
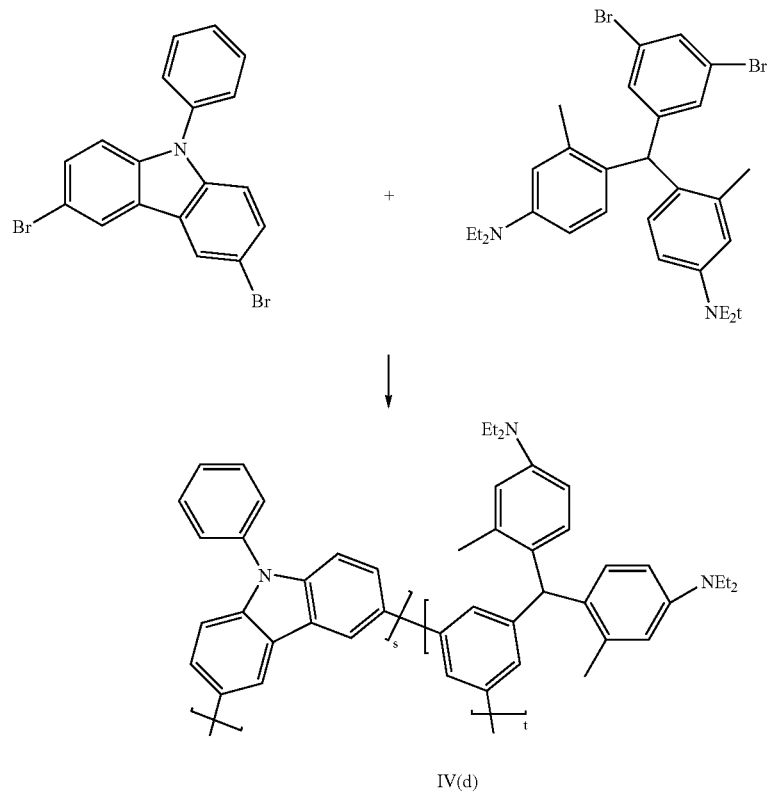
IV(d)

Example 4

This example illustrates the preparation of polymer IV(f), shown in FIG. 4.

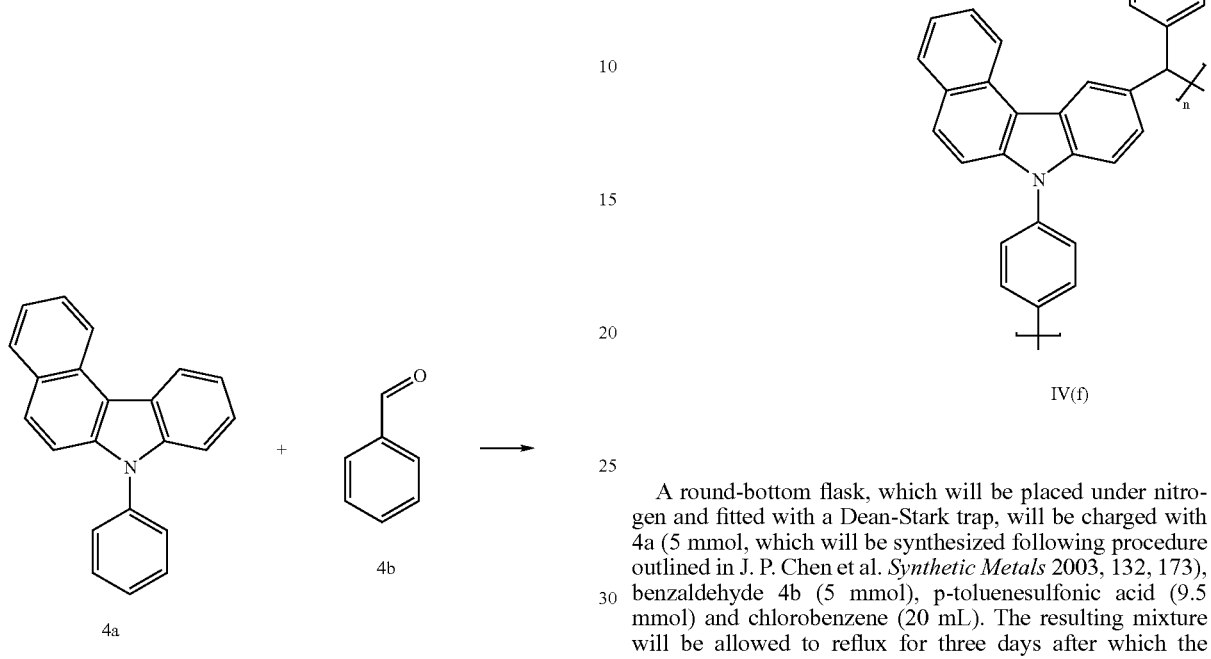

4a

4b

IV(f)

A round-bottom flask, which will be placed under nitrogen and fitted with a Dean-Stark trap, will be charged with 4a (5 mmol, which will be synthesized following procedure outlined in J. P. Chen et al. *Synthetic Metals* 2003, 132, 173), benzaldehyde 4b (5 mmol), p-toluenesulfonic acid (9.5 mmol) and chlorobenzene (20 mL). The resulting mixture will be allowed to reflux for three days after which the polymer will be isolated by precipitation from MeOH.

Example 5

This example illustrates the preparation of polymer IV(e) shown in FIG. 4.

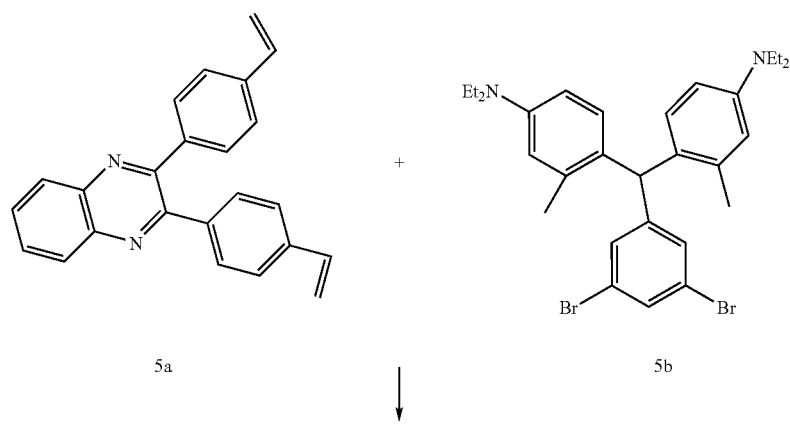

5a

5b

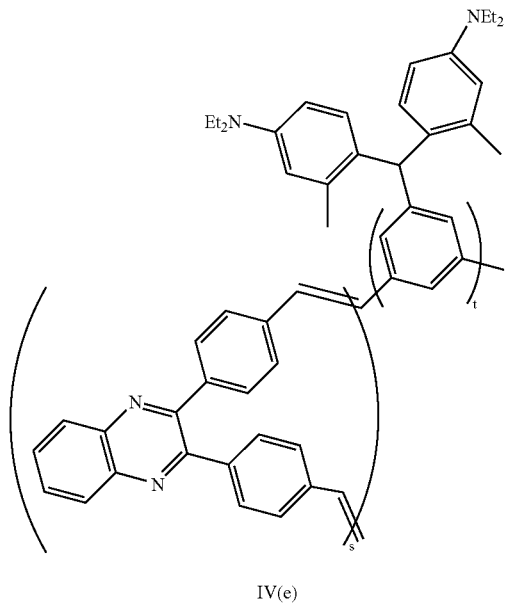

IV(e)

In an inert nitrogen atmosphere, a round-bottom flask was charged with 5a (0.5 mol), 5b (0.5 mol), Pd(OAc)$_2$ (0.05 mol), P(oTol)$_3$ (0.15 mol), Et$_3$N and DMF. The resulting mixture will be refluxed for three days and the product will be isolated by dilution with CH$_2$Cl$_2$ and precipitation from MeOH.

What is claimed is:

1. A composition comprising a polymer having a monomeric unit having a formula selected from the group consisting or Formulae IV(a), IV(b), IV(d) and IV(e),

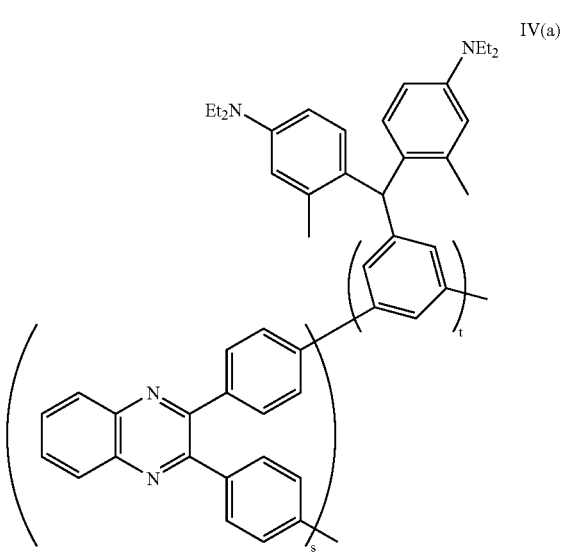

IV(a)

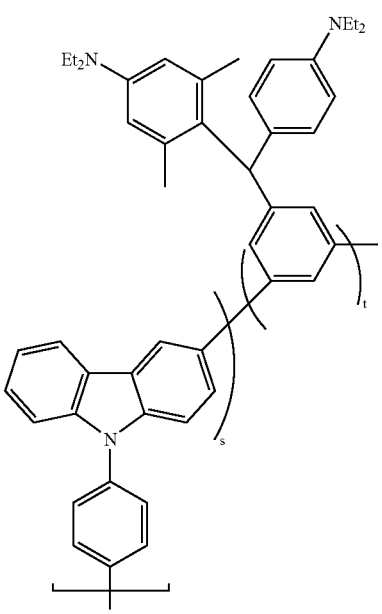

IV(b)

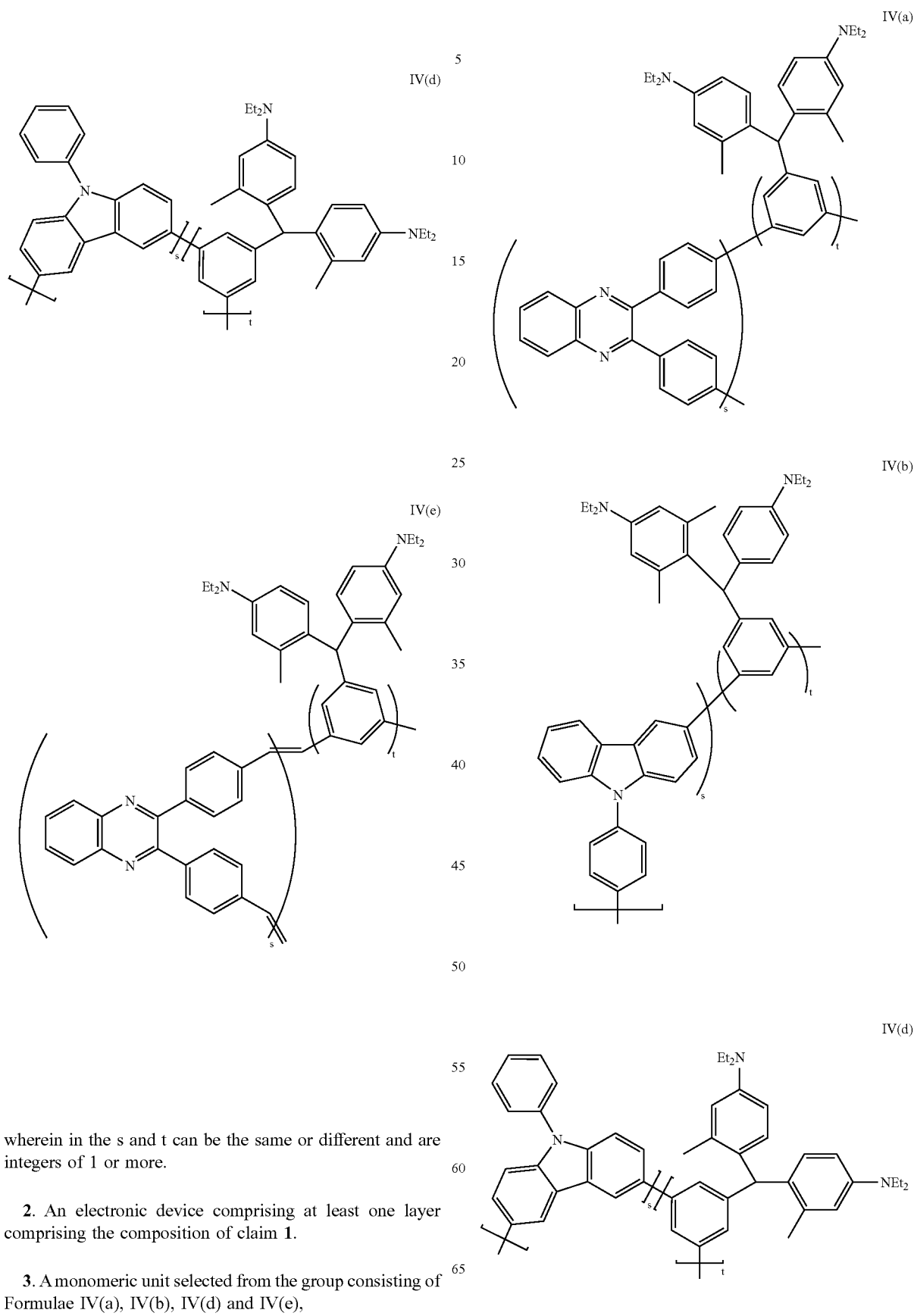
wherein in the s and t can be the same or different and are integers of 1 or more.
2. An electronic device comprising at least one layer comprising the composition of claim 1.
3. A monomeric unit selected from the group consisting of Formulae IV(a), IV(b), IV(d) and IV(e),

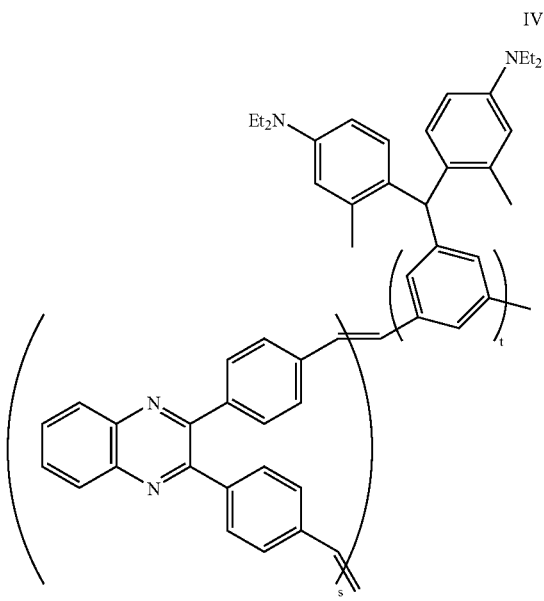
wherein in the s and t can be the same or different and are integers of 1 or more.
4. A polymer comprising at least one monomeric unit selected from the group consisting of Formulae IV(a), IV(b), IV(d) and IV(e),
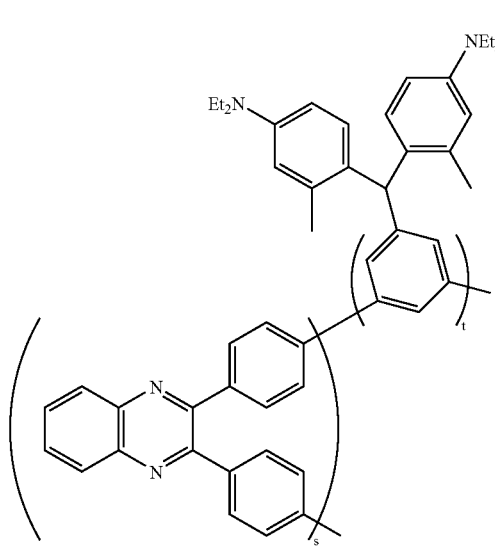
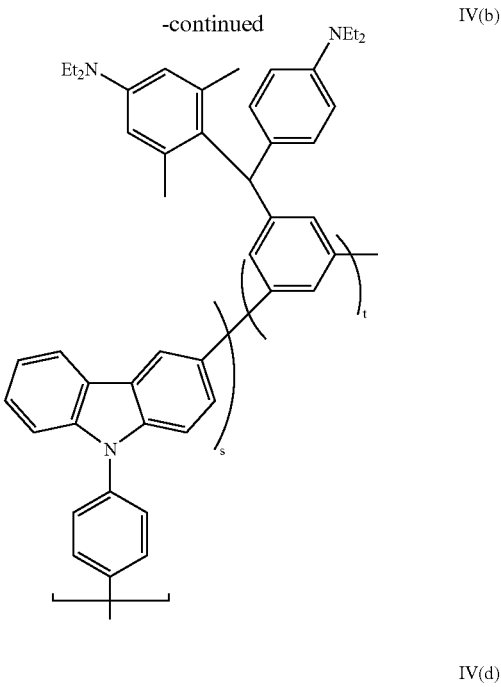
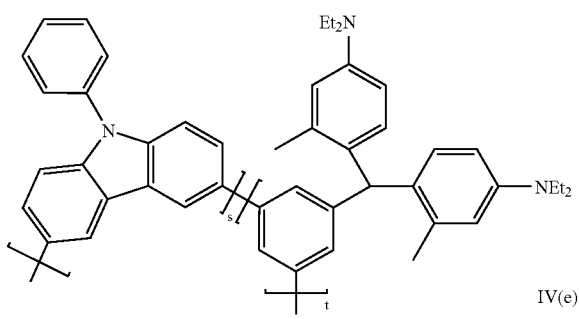
wherein in the s and t can be the same or different and are integers of 1 or more.
* * * * *